US011357214B2

United States Patent
Agarwal et al.

(10) Patent No.: US 11,357,214 B2
(45) Date of Patent: Jun. 14, 2022

(54) PIEZOELECTRIC SENSOR ASSEMBLY AND INTEGRATED BASE

(71) Applicants: Anuj Agarwal, Lexington, KY (US); Michael Lhamon, Lexington, KY (US); Kevin Donohue, Lexington, KY (US)

(72) Inventors: Anuj Agarwal, Lexington, KY (US); Michael Lhamon, Lexington, KY (US); Kevin Donohue, Lexington, KY (US)

(73) Assignee: Signal Solutions, LLC, Lexington, KY (US)

( * ) Notice: Subject to any disclaimer, the term of this patent is extended or adjusted under 35 U.S.C. 154(b) by 408 days.

(21) Appl. No.: 16/595,352

(22) Filed: Oct. 7, 2019

(65) Prior Publication Data
US 2021/0059219 A1    Mar. 4, 2021

Related U.S. Application Data

(63) Continuation-in-part of application No. 16/554,607, filed on Aug. 28, 2019.

(51) Int. Cl.
| | | |
|---|---|---|
| *A01K 29/00* | (2006.01) | |
| *A01K 1/00* | (2006.01) | |
| *A01K 1/015* | (2006.01) | |
| *A01K 1/03* | (2006.01) | |
| *G01L 1/16* | (2006.01) | |
| *A61B 5/113* | (2006.01) | |
| *A61B 5/00* | (2006.01) | |
| *A61B 5/0205* | (2006.01) | |

(52) U.S. Cl.
CPC .......... *A01K 29/005* (2013.01); *A01K 1/0035* (2013.01); *A01K 1/0157* (2013.01); *A01K 1/031* (2013.01); *A61B 5/0205* (2013.01); *A61B 5/113* (2013.01); *A61B 5/4812* (2013.01); *A61B 5/4818* (2013.01); *A61B 5/6887* (2013.01); *G01L 1/16* (2013.01)

(58) Field of Classification Search
None
See application file for complete search history.

(56) References Cited

U.S. PATENT DOCUMENTS

| | | | | |
|---|---|---|---|---|
| 5,178,013 A | * | 1/1993 | Suzuki | G01P 15/0907 73/12.04 |
| 2017/0356812 A1 | * | 12/2017 | Madden | G06F 3/04166 |

* cited by examiner

*Primary Examiner* — Adolf Dsouza
(74) *Attorney, Agent, or Firm* — Stockwell & Smedley, PSC

(57) ABSTRACT

A base for supporting a piezoelectric sensor which includes a generally planar support frame having an opening and a housing mounted in the opening. The housing has an upper portion including a sensor and a lower portion including a biasing member in contact with the sensor. The sensor is biased by the biasing force of the biasing member against the upper portion of the housing, whereby the upper portion is in turn biased by the biasing force against a floor of a cage positioned on the upper side of the support frame.

13 Claims, 12 Drawing Sheets

FIG. 7
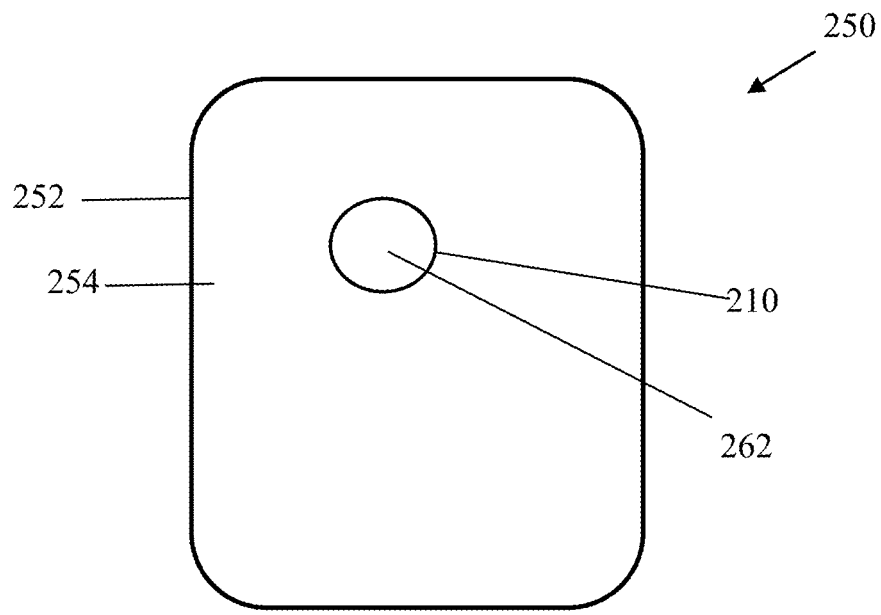
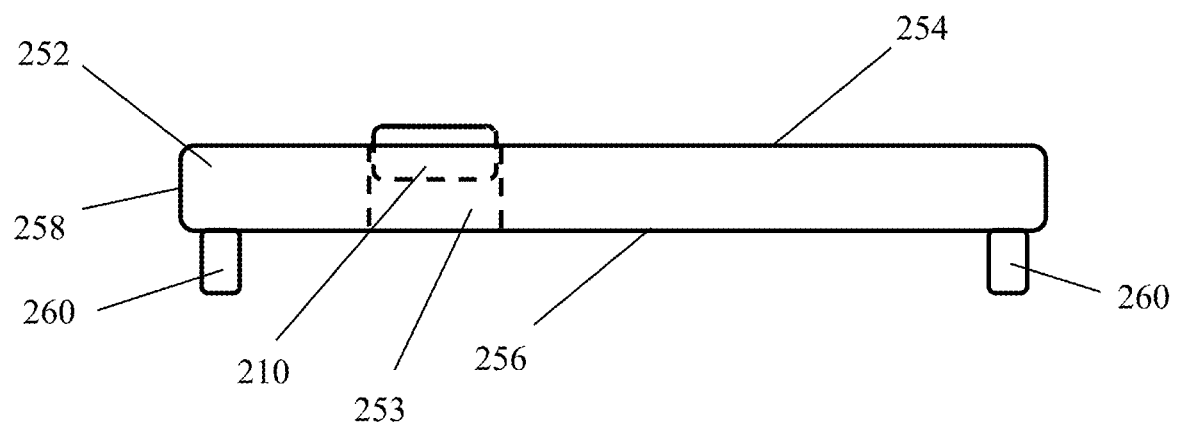
FIG. 8

Sensor1

Sensor2

Sensor1 − Sensor2

PIEZOELECTRIC SENSOR ASSEMBLY AND INTEGRATED BASE

CROSS REFERENCE TO RELATED APPLICATION

The application is a continuation in part of U.S. Nonprovisional patent application Ser. No. 16/554,607 filed on Aug. 28, 2019, the entire contents of which are incorporated herein by reference.

BACKGROUND OF THE INVENTION

The invention relates generally to the field of piezoelectric sensors and their use, and more particularly the invention is directed to a piezoelectric sensor including a composite sensor plate for sensing the activity of live subjects such as animals.

Bioelectric signals such as Electromyogram (EMG), Electroencephalogram (EEG), and Electrocardiogram (ECG) increase our understanding of the physiological mechanisms in the human body and can be measured externally by placing electrodes on the skin surface. However, acquiring biosignals in animals is not as straight forward as in humans, especially for rodents which are commonly used as models for human disease in medical research. Accordingly, determining physiological parameters by measuring biosignals is more complicated for non-human subjects, and often requires invasive placement of electrodes via surgery. For example, in rodents (rats, mice), bioelectric signals such as EEG and EMG are obtained from electrodes embedded surgically in their skull. Such surgery and post-surgery care limits application of such techniques for measuring biosignals to small scale studies. While noninvasive methods also exist, these are generally very expensive or have cumbersome equipment setup requirements which are incompatible with the animal's home cage. There are alternative, noninvasive methods for obtaining similar information revealed by measuring biosignals, such as video recording. However, these methods are also cumbersome to setup, have high implementation costs for large numbers of animals and generate a huge amount of data which poses management and efficiency challenges.

A piezoelectric sensor uses the piezoelectric effect to measure the changes in a physical quantity by converting it to an electrical charge. Piezoelectric sensors are available in different geometries such as film, cable, and discs of various geometries. Piezoelectric films and cable sensors are generally made of polyvinylidene fluoride (PVDF) and piezoelectric discs are commonly made of lead zirconate titanate (PZT). Piezoelectric devices have a wide range of application and broadly fit into four categories: generators (such as push button cigarette lighters and tire pressure monitoring sensors); sensors (such as flow sensor, thickness gauges and microphones); actuators (such as stack actuators and stripe actuators); and transducers (such as ultrasonic vibration generators for cleaning, atomizing liquids, drilling and medical diagnostics).

Existing piezoelectric sensors, such as piezoelectric disc sensors, include two wires or electrodes which act as a single-ended connection, where the voltage difference between the piezoelectric portion and the ground is detected and fed to an amplifier for further processing. These single ended connections suffer from electrical noise coupling into the sensor which corrupts the signal of interest.

Another issue is ensuring that the sensor of the invention can be used effectively with subject animals. New cages must be custom made to support sensors therein or existing cages must be modified, and liners are often necessary to protect the sensors from the subject animals.

As will be described herein, the invention relates to, but is not limited to, an integrated base for supporting a sensor, such as a piezoelectric sensor, which is constructed and configured to resolve the aforementioned issues and be advantageously used with a variety of chambers, cages and platforms and the use of such a sensor to noninvasively monitor physiological behaviors in live subjects.

SUMMARY OF THE INVENTION

Some embodiments of the invention are directed to a base for supporting one or more piezoelectric sensors comprising: a generally planar support frame having an upper side, a lower side, and one or more openings defined between the upper side and lower side; and a housing mounted in the opening, the housing including an upper portion and a lower portion, the upper portion including a sensor disposed therein and the lower portion includes a biasing member in contact with the sensor, wherein the sensor is biased by the biasing force of the biasing member against the upper portion of the housing, whereby the upper portion is in turn biased by the biasing force against a floor of a cage positioned on the upper side of the support frame.

A base of the invention provides many advantages, such as for example, eliminating a need to manufacture custom cages or modify existing cages to install sensors therein, because any commercially available animal cage may be used with a base of the invention and the sensors are biased to maintain contact externally with the bottom of the cage. In addition, the sensors are protected by the housing, and outside of the cage, thus eliminating the need for a plastic cage liner between the sensor and the animal.

Some embodiments of the invention are directed to at least one of the aforementioned one or more piezoelectric sensors comprising an insulator layer having opposing upper and lower surfaces; a first piezoelectric portion having a lower surface in contact with the upper surface of the insulator layer; a second piezoelectric portion having a lower surface in contact with the upper surface of the insulator layer; and an insulator strip dividing the first and second piezoelectric portions, wherein the first portion and second piezoelectric portion are laterally positioned with respect to one another in the same generally planar layer.

In some embodiments of the sensor of the invention, the first and second piezoelectric portions form a singular layer with two distinct electric signals.

In some embodiments of the sensor of the invention, the first and second piezoelectric portions are different sizes.

In some embodiments of the sensor of the invention, the first and second piezoelectric portions and insulator layer are shaped as discs.

In some embodiments of the sensor further comprises a wire connected to the first portion and a wire connected to the second portion for receiving electric signals from each portion.

In some embodiments of the sensor further comprises a wire connected to the insulator layer for receiving electric signal from the insulator layer.

In some embodiments of the sensor further comprises a signal amplifier connected to the wires.

In some embodiments of the sensor further comprises a covering material extending over the sensor and amplifier.

In some embodiments, the insulator layer and insulator strip are connected to one another.

In some embodiments, the insulator layer and insulator strip are brass.

In some embodiments, the first and second portions are ceramic.

Other embodiments, features and advantages of the invention will be readily appreciated and apparent from the following detailed description when considered in connection with the accompanying drawings.

BRIEF DESCRIPTION OF THE DRAWINGS

FIG. 7 is a top view of a base for supporting a sensor therein constructed and configured in accordance with an embodiment of the invention;

FIG. 8 is a side view of the base shown in FIG. 7;

DETAILED DESCRIPTION OF THE INVENTION

For illustrative purposes, the principles of the invention are described by referencing various exemplary embodiments. Although certain embodiments are specifically described herein, one of ordinary skill in the art will readily recognize that the same principles are equally applicable to, and can be employed in other systems and methods. Before explaining the disclosed embodiments of the present disclosure in detail, it is to be understood that the disclosure is not limited in its application to the details of any particular embodiment shown. Additionally, any terminology used herein is for the purpose of description and not of limitation. Furthermore, although certain methods may be described with reference to steps that are presented herein in a certain order, in many instances, these steps may be performed in any order as may be appreciated by one skilled in the art, and the novel method is therefore not limited to the particular arrangement of steps disclosed herein.

It must also be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably and the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, terms such as "mounted," "connected," "supported," "seated" and "coupled", and variations thereof, are used broadly and encompass both direct and indirect mountings, connections, supports, seating and couplings. Further, these terms are not restricted to physical or mechanical features. Unless otherwise apparent, or stated, directional references, such as "inner," "outer," "upper," "lower," "inward," "outward," and "side", and variations thereof, are intended to be relative to the parts described or orientation of a particular embodiment of the disclosure as shown in the first view of that embodiment, and are not limiting of the invention. Reference is now made to the figures wherein like parts are referred to by like numerals throughout.

Figure 1:
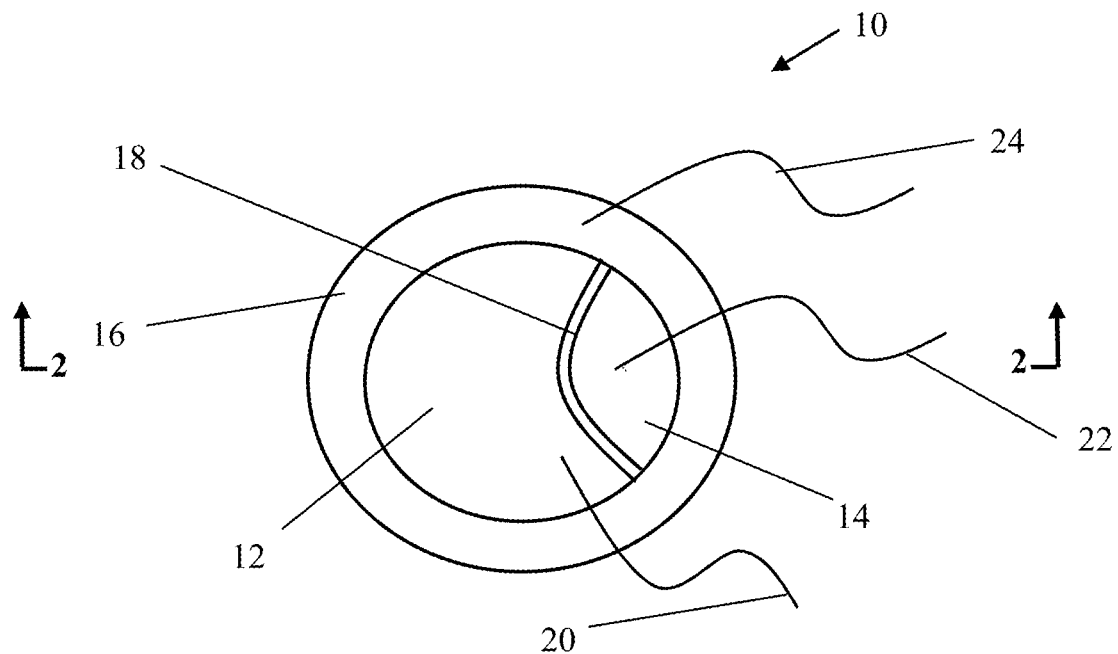
FIG. 1 is a top view of a piezo electric sensor constructed and configured in accordance with an embodiment of the invention.
Figure 2:
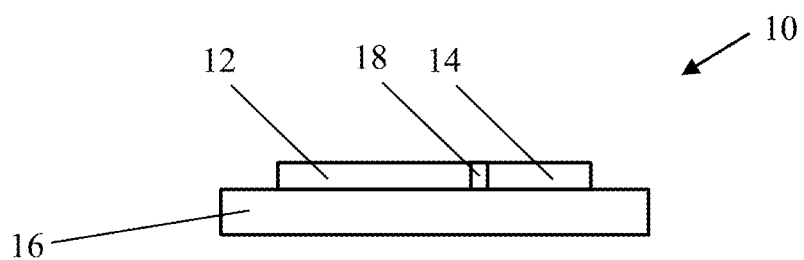
FIG. 2 is a cross sectional view of the piezo electric sensor of FIG. 1 taken along line 2-2.

Referring now to FIGS. 1 and 2, an exemplary embodiment of a piezoelectric sensor of the invention is generally identified by reference number 10. In this embodiment, sensor 10 has an overall circular shape whereas in other embodiments, sensor 10 may be of a different form.

Sensor 10 includes a first piezoelectric portion 12 and a second piezoelectric portion 14. Each portion 12 and 14 has a lower side in contact with an upper side of the non-piezoelectric or insulative layer or ground 16. In this embodiment, portions 12 and 14 form a single planar layer relative to one another, with both being in contact with the same surface of layer 16. Portions 12 and 14 are maintained apart from one another by an insulative or ground dividing strip 18, which may be part of or the same material as layer 16. Strip 18 is within the same plane as portions 12 and 14 and thus divides piezoelectric portions 12 and 14 laterally from one another within the same plane, thus keeping them electrically separated to deliver distinct signals, and maintaining the same overall sensor profile. Wires or electrodes 20 and 22 are in electrical communication with piezoelectric portions 12 and 14, respectively, to receive these distinct electrical signals. Electrode 24 is in electrical communication with layer 16 (and/or in some embodiments, strip 18) to be maintained as a ground.

In operation, the three-wire electrode sensor 10 is configured as a differential connection, wherein the voltage or charge difference between the two distinct signal sources, portions 12 and 14, are input into a difference amplifier (not shown). Coupled electrical noise interferes with both signals which is common to both input signals is cancelled by the amplifier. Sensor 10 is thus less susceptible to noise pick-up as compared with two wire sensors.

Figure 3:
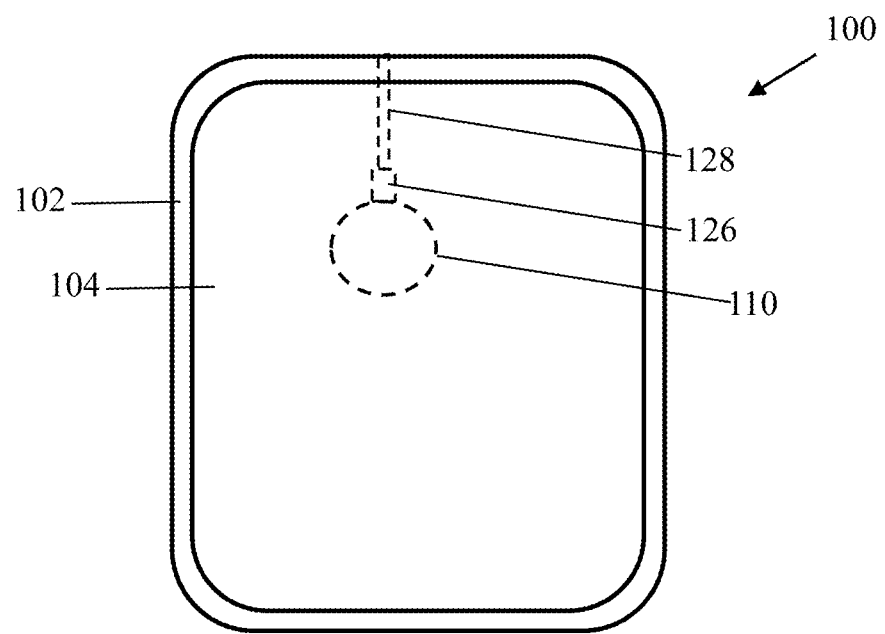
FIG. 3 is a top view of an animal housing in which a sensor of the invention is deployed.

FIG. 3 illustrates a sensor 110 of the invention attached to the bottom 104 of a cage or housing 100 having walls 102. Sensor 110 is connected with an amplifier 126 and wire bundle 128 containing wires connected to the two piezoelectric portions (not shown) and the ground (not shown). It should be understood that the piezo sensor 110 can be located anywhere in the vicinity of the animal cage 100, for example inside the cage, on the side wall, on the lid of the cage, embedded in the wall, etc. Also note that the piezo disc sensor can be attached to the cage in several ways, for example, using liquid adhesive, tape, magnets, screws, etc. The piezo disc sensor 110 could also be present on a separate base (or platform) against which a cage is made to rest.

It should also be understood that the piezo disc sensor 110 may be embedded in a material, such as a plastic or elastomer, such as polyurethane, along with differential amplifier 126. The sensor and amplifier housing may be attached to the bottom of the cage using a magnet. The magnet used to attach the sensor housing can be of varying sizes, shapes, and thickness and can be fixed to the cage in several ways (glued, embedded, paint, etc.) In some embodiments, sensor 110 and amplifier housing 126 can be made from different materials and can be 3D printed, molded, carved, stitched, etc.

While the exemplary embodiments herein describe wired transmission of data from the piezo disc sensor 10 and 110. It should be understood that the transmission of data may be wireless. For large scale applications, the piezo disc sensors of the invention can also be attached to cage racks housing more than 90 cages instead of individual cages, such as cage 100. Depending on the type of rack, the disc sensor of the invention can be either directly or indirectly attached to the cage or can be present on the rack itself. It should be readily apparent that more than one disc sensor of the invention may be present on the cage. For example, multiple sensors on a single cage are useful when there are either a) multiple animals in a single cage or b) there is a need to track the location of a single animal within the cage. In some applications one of the disc sensors of the invention may be specifically used as a reference for noise cancelling applications.

Figure 4A:
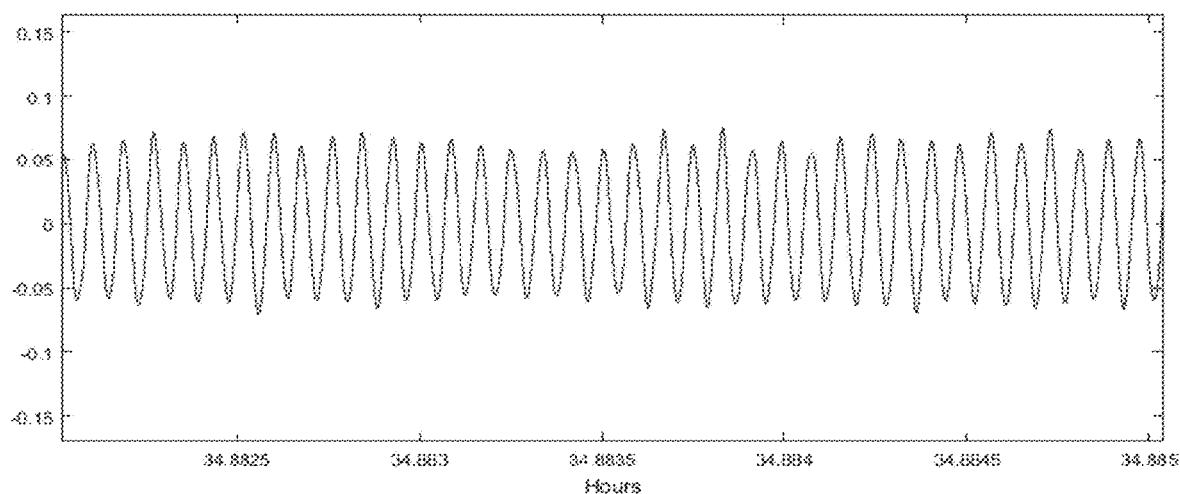
FIGS. 4A and 4B provide Piezo signals as obtained from (A) a piezoelectric film and (B) a piezoelectric disc sensor attached to a mouse cage. The film sensor was located over the cage floor and the disc sensor under the cage floor. The cage floor was made of a 5 mm thick polycarbonate material.
Figure 4B:
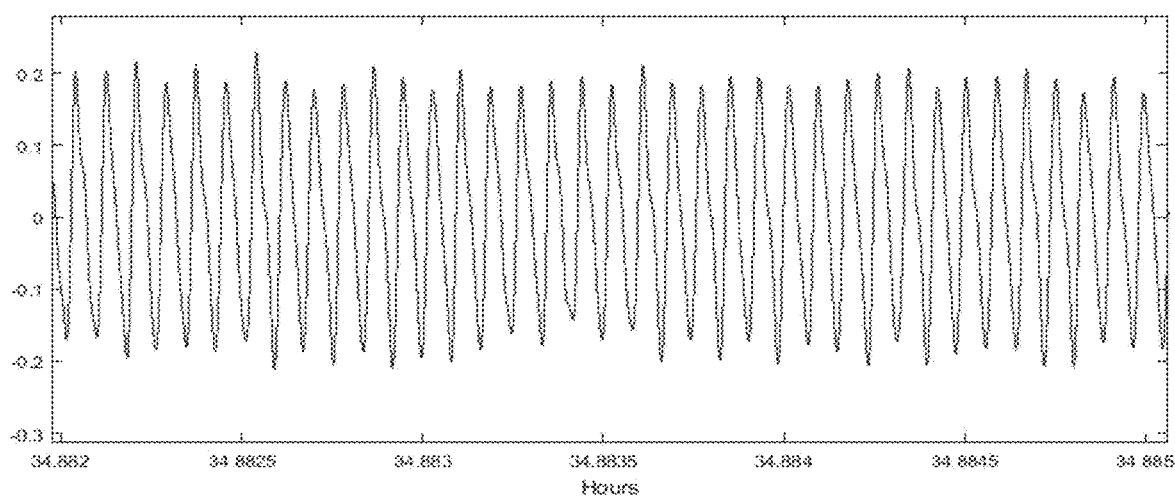

FIGS. 4A and 4B provide comparisons of the signal quality between a piezo film (FIG. 4A) and a piezo disc sensor of the invention (FIG. 4B). Both the film and disc sensors of the invention were attached to a mouse cage. The film sensor was located over the cage floor (made of 5 mm thick polycarbonate sheet) and the disc sensor was located under the cage floor. The data represents a section where the mouse was sleeping inside the cage. When the animal is stationary (like during sleep), the piezo sensors capture the pressure changes due to the periodic movement of the thorax and the displacement of air from the nostrils, occurring due to inhalation and exhalation during breathing. FIGS. 4A and 4B contain about 12 seconds of data, which have about 36 periods of breaths, translating to a respiratory rate of 3 Hz (breaths per second). The data in FIGS. 4A and 4B illustrate that in comparison to a piezo film sensor, the piezo disc sensor of the invention is equally sensitive to mouse behaviors in a cage. The disc sensor is also substantially less expensive to manufacture. The disc sensor of the invention costs $1.60 as compared to a piezo film (about $100) or cable sensor (about $36) and is more widely available commercially.

Figure 5:
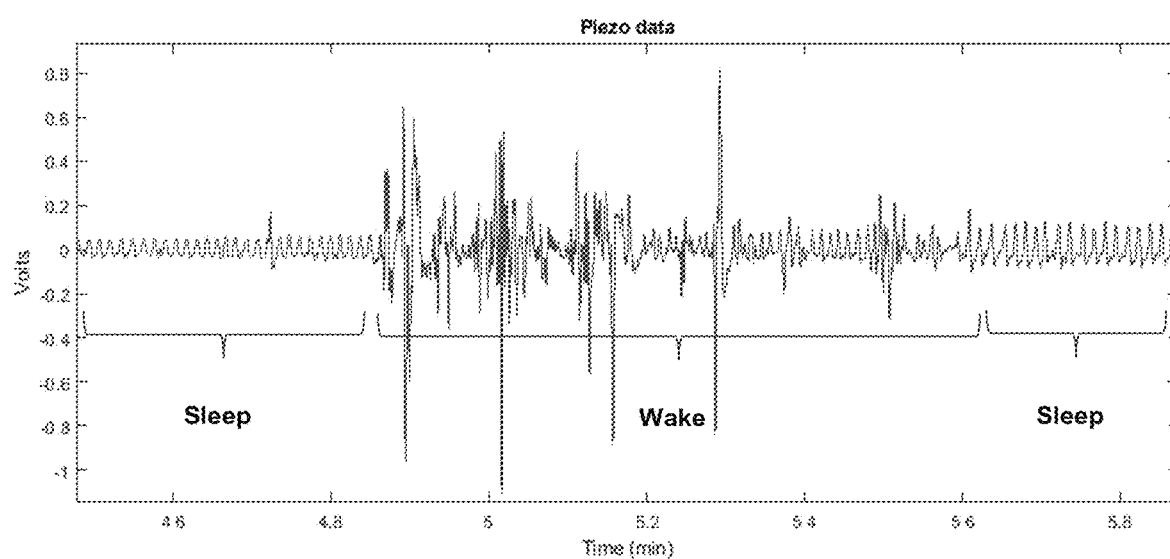
FIG. 5 shows an example of a piezo signal obtained from a rat, where the animal is first sleeping, then wakes up briefly, and goes back to sleep, using a sensor of the invention.

FIG. 5 shows an example of a piezo signal obtained from a rat, where the animal is first sleeping, then wakes up briefly, and goes back to sleep during Sleep, the signal amplitude is low and periodic in nature. When the animal is awake and moving, the signal amplitude is higher but irregular (not periodic).

Figure 6:
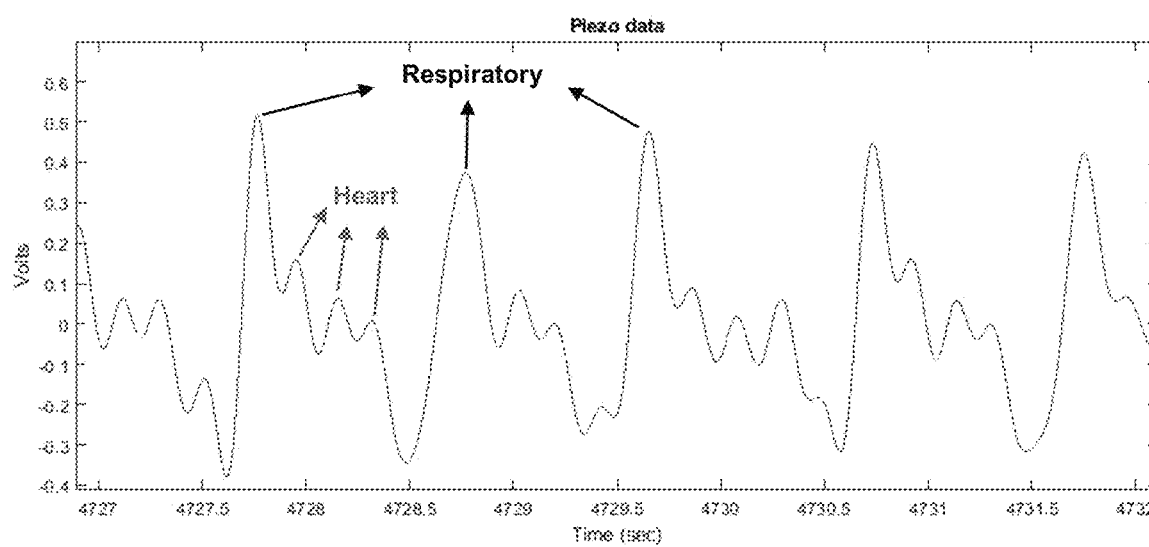
FIG. 6 illustrates piezo signals obtained from a rat using a piezo disc sensor of the invention.

FIG. 6 shows 5 seconds of data obtained from a rat, during sleep. The piezo signal consists of some big peaks corresponding to respiration, and some small peaks corresponding to the beating of the heart. For both the large peaks and the small peaks, the inverse of the inter peak distance gives estimates of the respiratory rate and the heart rate. As shown in the figure, there are 5 big peaks and 20 big+small peaks occurring over 5 seconds, which yields a breath rate of 1 Hz (breaths per second) and a heart rate of 4 Hz (beats per second) for this rat.

Thus, as described herein a piezo disc sensor of the invention enables noninvasive detection of sleep, Activity, breathing rates, and heart rates. The sensor of the invention can also be used for detection of epilepsy and sleep apneas. For example, epilepsy is marked by distinct changes in animal posture and movement, which can be captured by the piezo disc sensor of the invention. Sleep apnea is exhibited by a long pause in breathing during sleep, which can also be captured using the piezo disc sensor of the invention. It should be understood that the use of the piezo disc sensor of the invention is not limited to sleep, activity, breath rates, and heart rates, in that there may be many other potential applications of the sensor of the invention.

FIGS. 7-8 illustrates a base 250 constructed in accordance with another embodiment of the invention. Base 250 includes a support frame 252 having an upper side 254, an opposing lower side 256 and a side wall 258. While frame 252 is depicted as generally rectangular in shape, it should be understood that frame 252 may be constructed in various other shapes as well.

Figure 9:
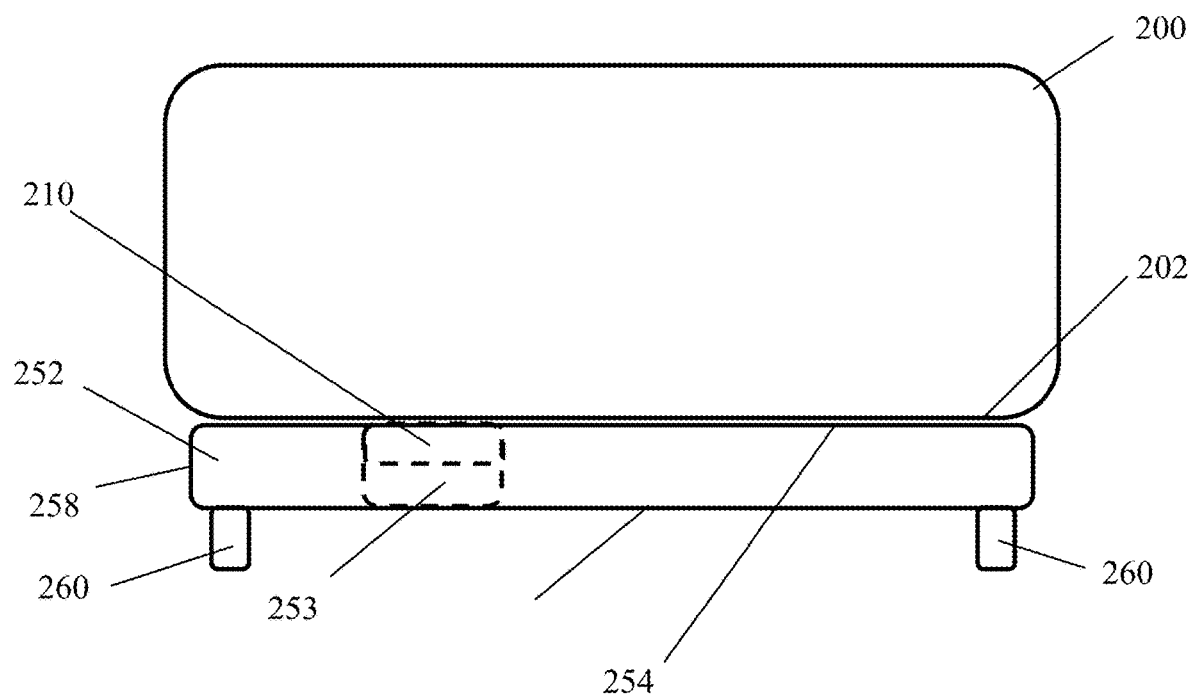
FIG. 9 is a side view of a base as shown in FIG. 7 with a cage positioned on the upper side of the base.
Figure 10:
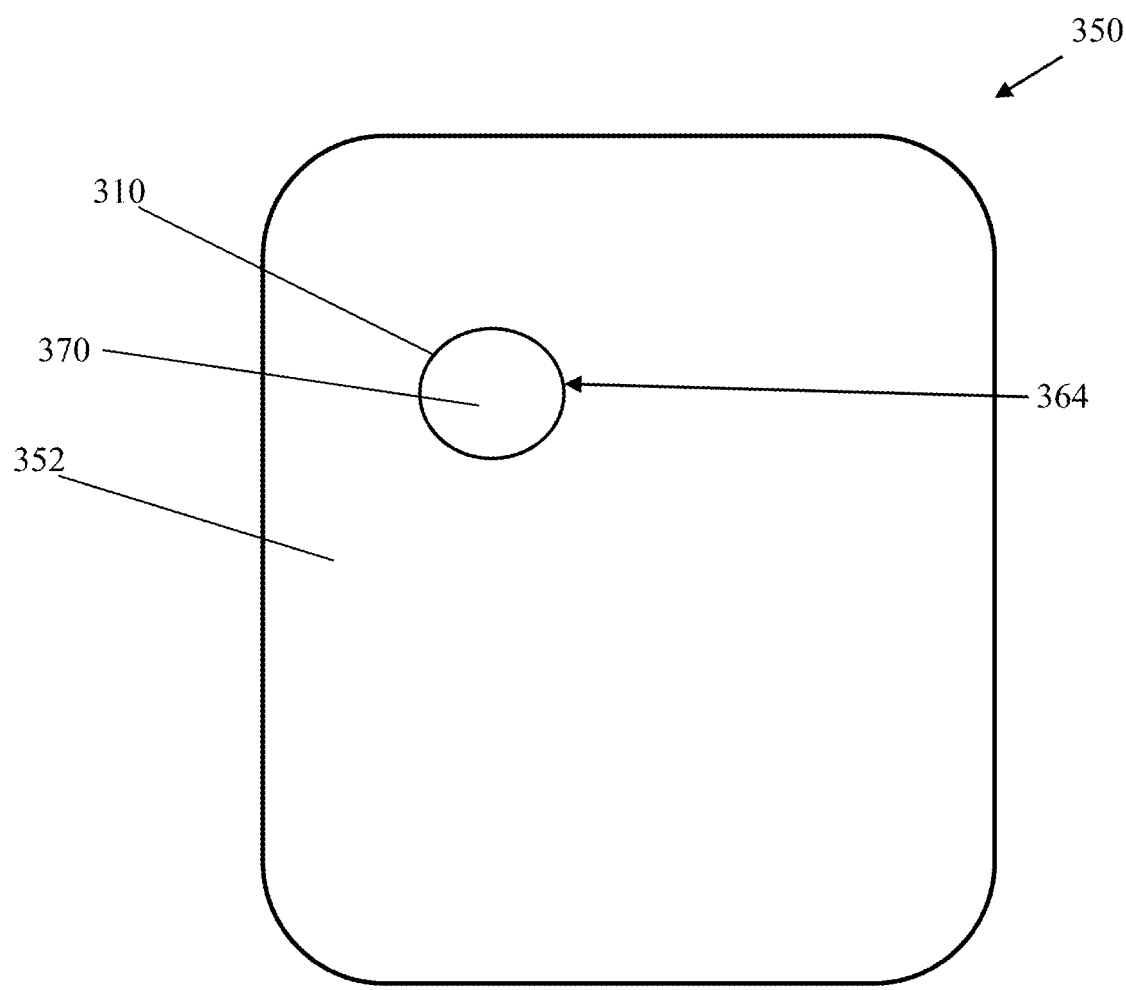
FIG. 10 is a top view of a base for supporting a sensor within a sensor housing therein constructed and configured in accordance with another embodiment of the invention.
Figure 11:
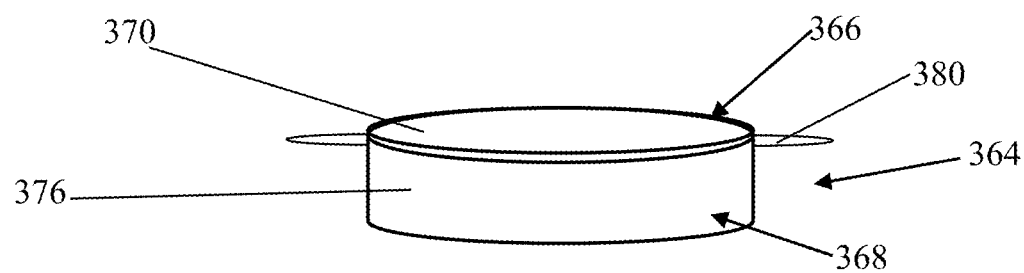
FIG. 11 is front perspective view of a sensor housing constructed in accordance with the invention.
Figure 12:
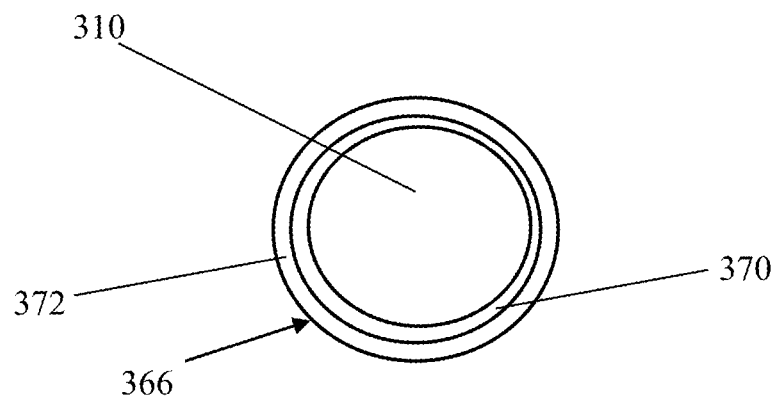
FIG. 12 is top view of an upper housing portion of the sensor housing shown in FIG. 11.
Figure 13:
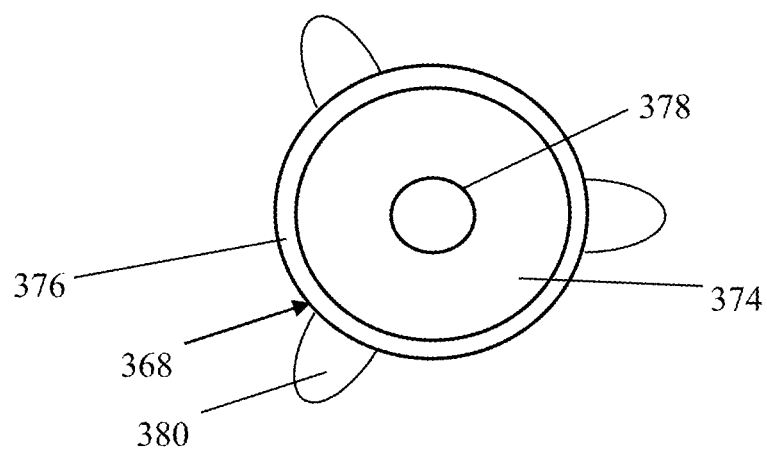
FIG. 13 is top view of a lower housing portion of the sensor housing shown in FIG. 11.
Figure 14:
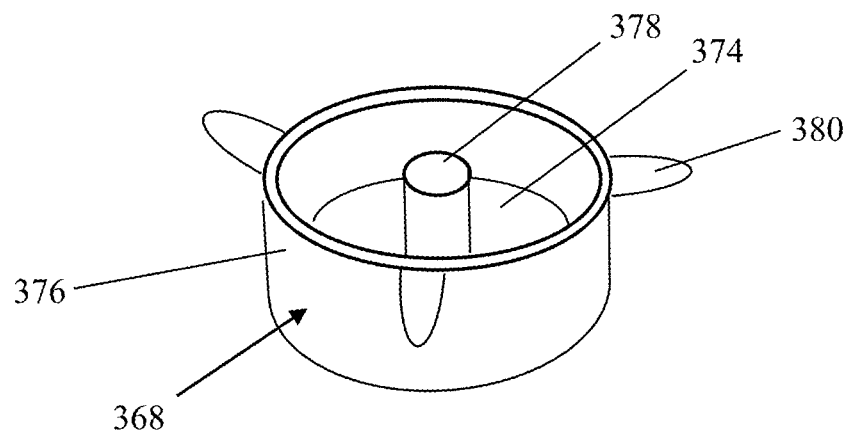
FIG. 14 is top perspective view of a lower housing portion of the sensor housing shown in FIG. 11.
Figure 15:
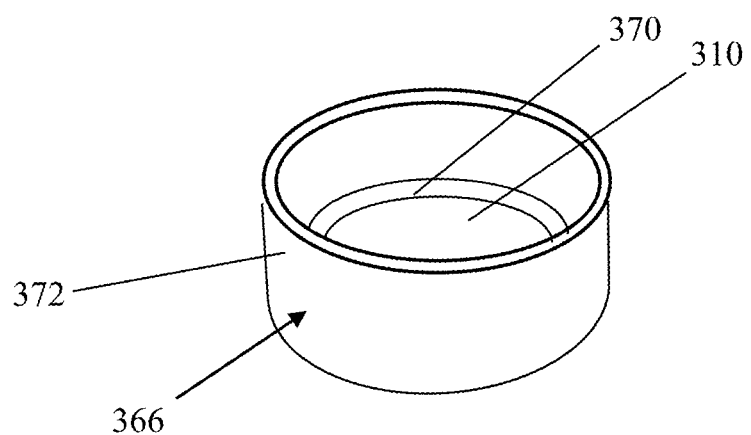
FIG. 15 is top perspective view of an upper housing portion of the sensor housing shown in FIG. 11.

In some embodiments base 250 is constructed as part or all of the bottom or floor of an animal enclosure or cage. In the embodiment depicted herein, frame 252 is configured to be inserted to replace or be seated in or as shown in FIG. 9, under an existing enclosure 200 having a bottom 202. In some embodiments, enclosure 200 includes exterior features at the bottom 202, such as parallel or transverse ridges. Upper side 254 of base 250 may include complementary or corresponding features which cooperate with the exterior features of bottom 202 to facilitate seating and partially securing enclosure 202 on frame 252. Upper side 254 may also be shaped or include surface features for receiving and seating thereon different shapes of a bottom 202.

Base 250 further includes four support legs 260 projecting from lower side 256. In this embodiment, the elevation of support frame 252 enabled by support legs 260 elevates support frame 252 above a floor, which may be a floor, which may be a bottom 202 should base 250 be positioned with an enclosure 200, or an exterior floor (not shown) when base 250 is positioned outside of an enclosure 200.

A sensor 210, which may be the same or similar to sensors 10 or 110 described above is mounted in frame 252. In some embodiments, sensor 210 is connected frame 252 such that the upper surface 262 of sensor 210 is planar with upper side 254 of frame 252. Sensor 210 may be mounted within a cut-out, opening or sensor receiving port 253 in frame 252, which may extend between upper side 254 and lower side 256. In some embodiments, sensor 210 is underneath upper side 254 or otherwise covered by a substrate or membrane (not shown) which is substantially planar with upper side 254. In some embodiments, sensor 210 is biased so that upper surface 262 is forced into contact and against upper side 254, the substrate or membrane, as applicable, or as in this embodiment shown in FIG. 8, upper surface 262 projects above upper side 254 of frame 252 due to the biasing force. As shown in FIG. 9, the weight of enclosure 200 may counteract the biasing force on sensor 210 such that the upper surface of 262 of sensor 210 is almost, close to, or substantially planar with upper side 254 of frame 252 when enclosure 200 is seated on upper side 254 while still maintaining the biasing force causing contact between upper surface 262 and bottom 202 of enclosure 200.

The size, shape and design of sensor 210, as well as its position in frame 252, are not limited to the configuration as shown. It should also be understood that other elements, such as wires, power sources, signal conditioners, etc., are not shown in the figure for ease of illustrating a base constructed in accordance with the invention.

A sensor 310 may be disposed in a housing 364 which is then attached to a receiving port or opening 353 in frame 352 of a base 350 as shown in FIGS. 10-16. Housing 364 may be attached to frame 352 by any conventional means such as by the use of mechanical fasteners or adhesives. In this embodiment, housing 364 includes an upper housing portion 366 and a lower housing portion 368 which cooperate with one another and sensor 310 such that sensor 310 can be placed in upper portion 366 and upper portion 366 can be seated in lower portion 368.

It should be understood that housing 364 and thus upper portion 366 and lower portion 368 may be of any size or shape. In this embodiment, upper portion 366 and lower portion 368 are tubular in shape, and in particular, tube-shaped with closed ends. Upper portion 366 includes a circular end 370 and side wall 372. Lower portion 368 includes a circular end 374 and side wall 376. Lower portion 368 further includes a biasing member 378 which may be a spring. Lower portion 368 further includes mounting brackets 380 for facilitating attachment with frame 352.

Figure 16:
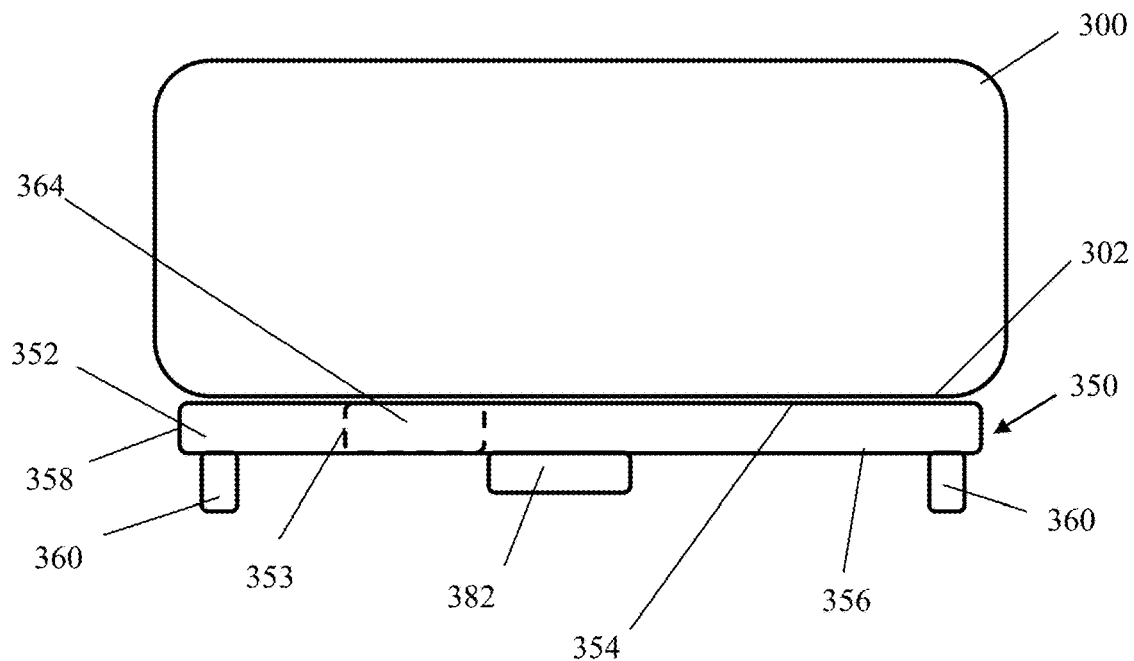
FIG. 16 is a side view of the base shown in FIG. 10 with a cage positioned on the upper side of the base.

As shown in FIG. 16 a cage 300 is seated on base 350. Housing 364 with a sensor 310 disposed inside is mounted on frame 352 such that the sensor 310 is biased by biasing member 378 to be forced against end 370 of upper portion 368, which in turn forces against, and maintains desirable surface contact with, bottom 302 of cage 300. Sensor 310 may be connected with (wired or wirelessly) other sensing devices, elements and apparatus, such as a signal conditioning unit 382 mounted on lower side 356 of frame 352. Sensor 310 may be any sensor, such as a piezo electric sensor such as sensor 10 or 110.

Figure 17:
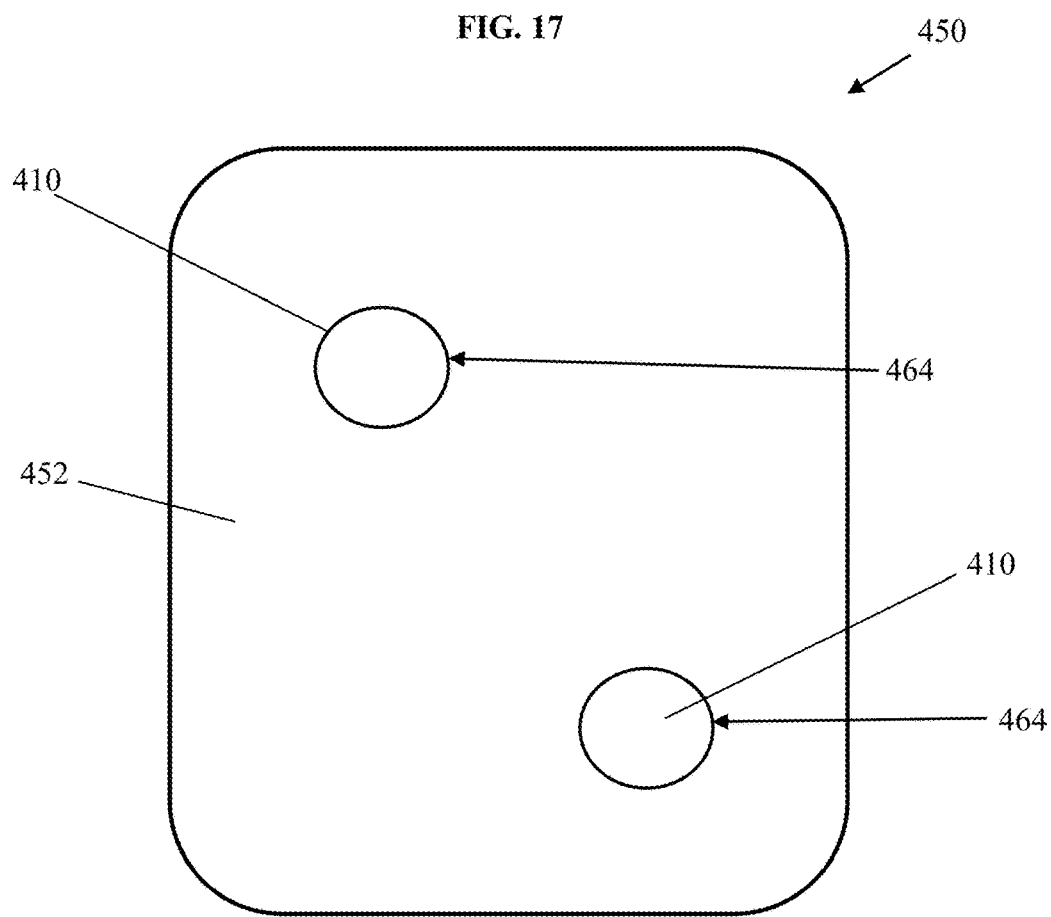
FIG. 17 is a top view of a base constructed and configured in accordance with another embodiment of the invention, illustrating among other things, a diagonally opposing sensor configuration.

A base, frame and housing of the invention may be made of many suitable materials, such as plastic (e.g., acrylic, polycarbonate, etc), aluminum or steel. A base of the invention may be configured to accommodate multiple sensors and/or housings with sensors therein, in any configuration, of any size, number and shape. For example, FIG. 17 illustrates a base 450 with frame 452 including housings 464 with sensors 410 therein. Housings 464, and therefore, sensors 410, are positioned on diagonally opposite areas of frame 452 to enable greater sensor detection and signal receiving from the entire cage.

In this embodiment a sensor 410 may be connected for communication via a cable to a data acquisition unit containing an analog-to-digital converter and additional signal processing hardware. The data acquisition unit is then connected to the computer via a USB cable. A data acquisition software on the computer is then used to capture data from the sensors.

Figure 18A:
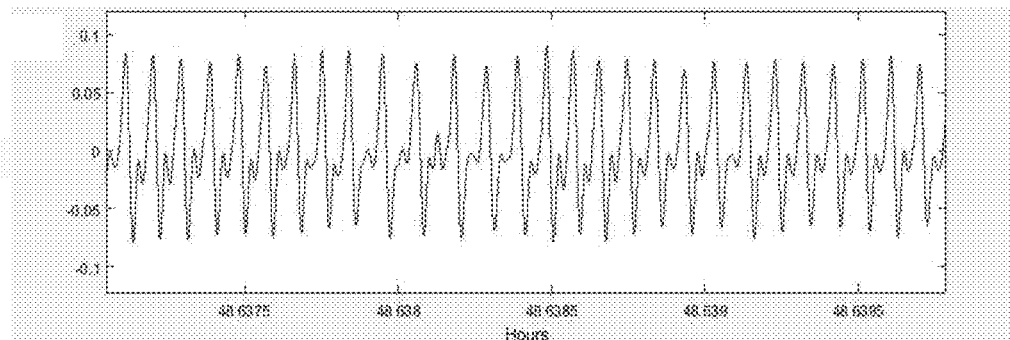
FIG. 18A-C provide examples of signal capture when an animal is present closer to sensor-1 in a sensor base configuration as shown in FIG. 17, wherein FIG. 18A provides graphed signals captured from sensor-1, with amplitude range ±0.08 volts, FIG. 18B provides graphed signals captured from sensor-2, with amplitude range ±0.003 volts, and FIG. 18C provides the graphed difference of signals from sensor-1 and sensor-2, illustrating among other things, that the difference signal is dominated by the signal in sensor-1.
Figure 18B:
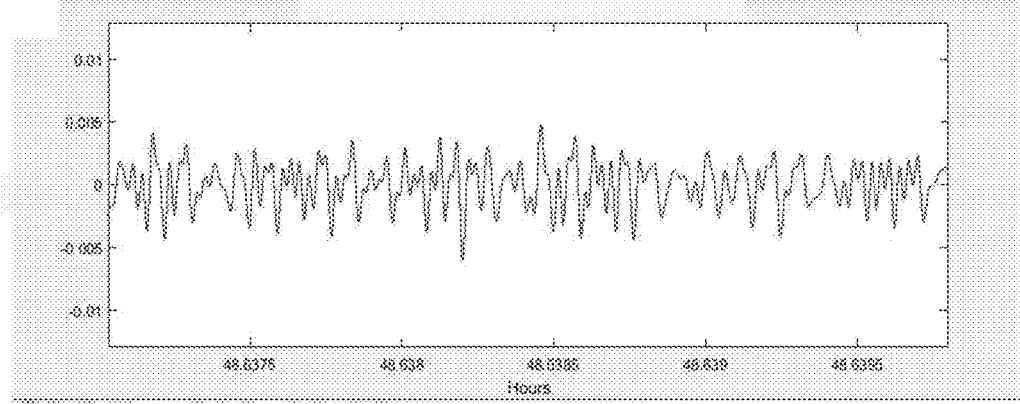
Figure 18C:
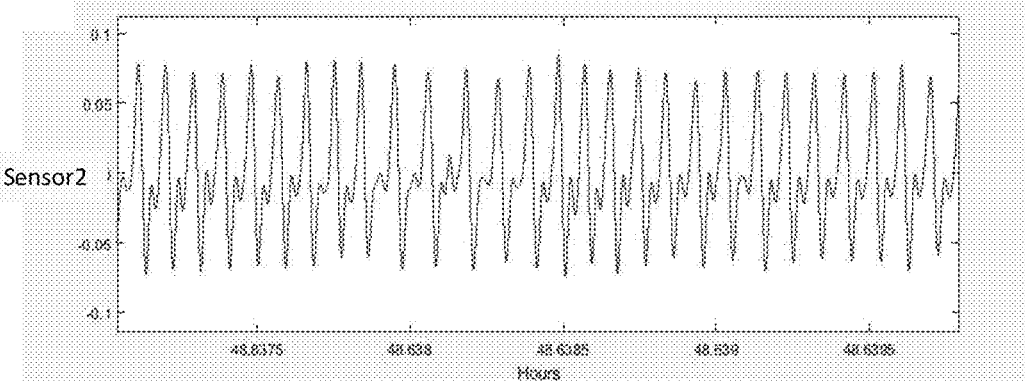

FIG. 18A-C shows examples of piezo signals recorded from a mouse using a base of the invention, such as base 450 which includes two sensors, such as sensors 10 or 110, positioned at diagonally opposing ends of support frame 452, which are referred to in this description as sensor-1 and sensor-2. The data shown in FIG. 18A-C was taken from a period when the mouse was sleeping closer to sensor-1. FIG. 18A shows the signal obtained from sensor-1, where the signal amplitude varied between ±0.08 volts. FIG. 18B contains the signal from sensor-2, where the signal amplitude varied between ±0.003 volts. FIG. 18C contains the difference of signals from sensor-1 and sensor-2. The difference signal is dominated by the signal in sensor-1, since the amplitude of the signal picked up from sensor-1 is almost 27 folds higher than the amplitude of the signal picked up from sensor-2.

Figure 19A:
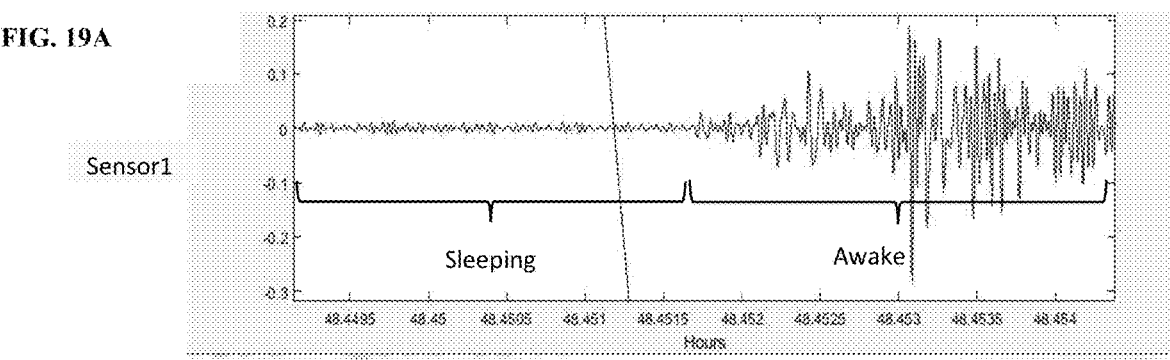
FIG. 19A-C provide examples of signal capture when an animal was first present closer to sensor-2 and then moved closer to sensor-1 in a sensor base configuration as shown in FIG. 17, wherein FIG. 19A provides graphed signals captured from sensor-1, with amplitude range ±0.3 volts, FIG. 19B provides graphed signals captured from sensor-2, with amplitude range ±1.5 volts, and FIG. 19C provides the graphed difference of signals from sensor-1 and sensor-2, illustrating among other things, that the difference signal captures the movement of the animal across the cage.
Figure 19B:
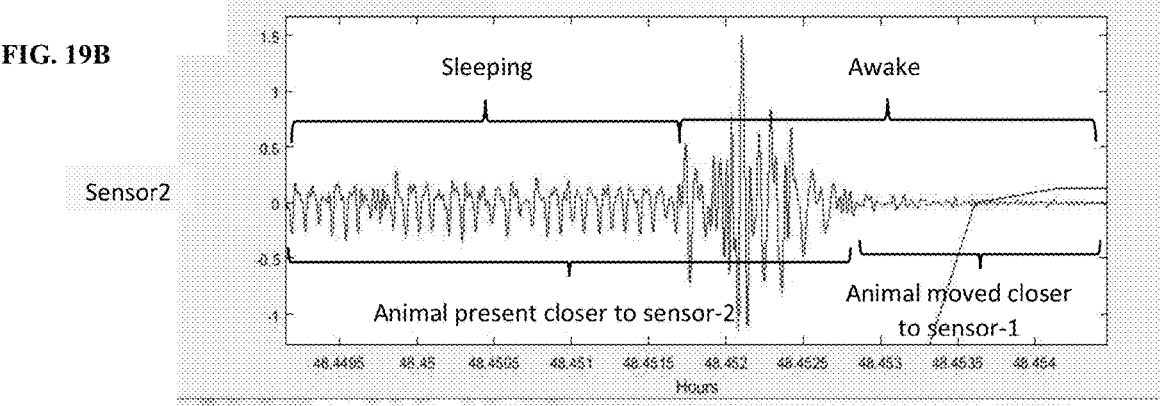
Figure 19C:
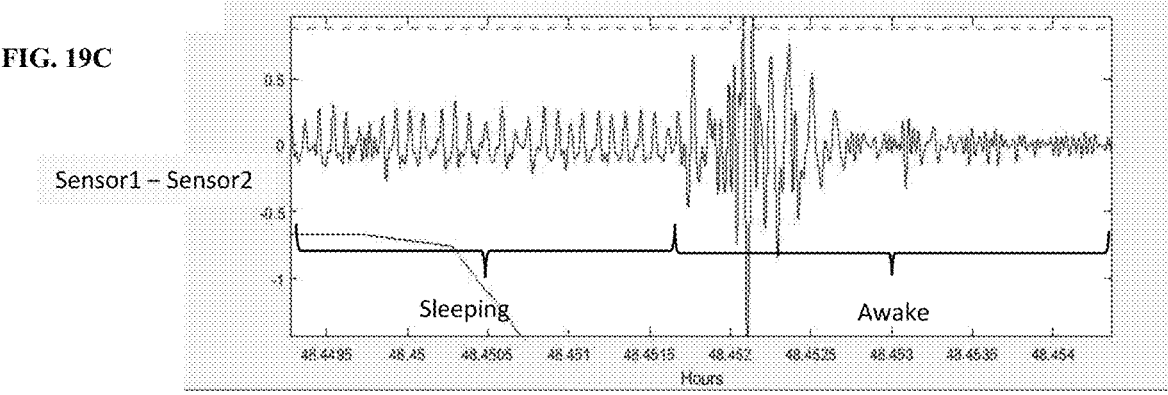

FIG. 19A-C shows examples of piezo signals taken from a period where the mouse was first sleeping, closer to sensor-2, and then woke up and moved towards sensor-1. FIG. 19B shows the signal obtained from sensor-2, where the animal was first sleeping and then woke-up. After waking up, the animal moved closer to sensor-1, leading to a drop in the signal amplitude. Similarly in FIG. 19A, the signal amplitude is first lower, until the animal is closer to sensor-1, and then increases towards the end, when the animal wakes up and comes towards sensor-1. FIG. 19C shows the difference of signals from sensor-1 and sensor-2, where the signal in the first part (until the animal wakes up) is dominated by sensor-1 signal and the signal in the second part (after waking up) is dominated by sensor-2 signal. Thus the difference signal captures the presence of the animal across the cage.

FIGS. 18A-C and 19A-C demonstrate the use of the base of the invention to track the presence and movement of the animal across the cage. In base 450, the difference of the signals, obtained from each sensor, can be used to noninvasively monitor the physiological parameters of the animal. Subtraction of the signals from each sensor also helps in subtracting out the unwanted noise, which gets picked up (almost equally) by both sensors. In certain cases, the signals from each cage can also be added and used to track parameters such as activity levels which can be used for general health monitoring of mice.

In applications where multiple animals are housed in one cage, multiple sensors can be integrated in the cage base and signal processing techniques such as independent component analysis can be applied to separate signals coming from each animal. Each separated signal can then be analyzed individually to determine the physiological parameters. Such applications can be used for general health monitoring of group housed animals.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Other aspects and features of the invention can be obtained from a study of the drawings, the disclosure, and the appended claims. The invention may be practiced otherwise than as specifically described within the scope of the appended claims.

Although specific features of various embodiments of the invention may be shown in some drawings and not in others, this is for convenience only. In accordance with the principles of the invention, any feature of a drawing may be referenced and/or claimed in combination with any feature of any other drawing.

While exemplary devices, apparatus, systems and methods of the invention have been described herein, it should also be understood that the foregoing is only illustrative of a few particular embodiments with exemplary and/or preferred features, as well as principles of the invention, and that various modifications can be made by those skilled in the art without departing from the scope and spirit of the invention. Therefore, the described embodiments should not be considered as limiting of the scope of the invention in any way. Accordingly, the invention embraces alternatives, modifications and variations which fall within the spirit and scope of the invention as set forth by the claims and any equivalents thereto.

The invention claimed is:

1. A base for supporting a piezoelectric sensor against a floor of a cage configured to contain a live subject, the base comprising:
    a generally planar support frame having an upper side, a lower side, and an opening defined between the upper side and lower side, wherein the cage is seated on the support frame whereby the floor of the cage is in contact with the upper side of the support frame; and
    a housing mounted in the opening, the housing including an upper portion and a lower portion, the upper portion including a sensor disposed therein and the lower portion includes a biasing member in contact with the sensor, the upper portion contacting the floor of the cage, wherein the sensor is continuously biased by the biasing force of the biasing member against the upper portion of the housing, whereby the upper portion is in turn biased by the biasing force against the floor of the cage seated on the support frame.

2. A base as recited in claim 1, wherein the piezoelectric sensor comprises:
    an insulator layer having opposing upper and lower surfaces;
    a first piezoelectric portion having a lower surface in contact with the upper surface of the insulator layer;
    a second piezoelectric portion having a lower surface in contact with the upper surface of the insulator layer; and
    an insulator strip dividing the first and second piezoelectric portions,
    wherein the first portion and second piezoelectric portion are laterally positioned with respect to one another in the same generally planar layer.

3. The piezoelectric sensor of claim 2, wherein the first and second piezoelectric portions form a singular layer with two distinct electric signals.

4. The piezoelectric sensor of claim 2, wherein the first and second piezoelectric portions are different sizes.

5. The piezoelectric sensor of claim 2, wherein the insulator layer is shaped as a disc.

6. The piezoelectric sensor of claim 2, further comprising a wire connected to the first portion and a wire connected to the second portion for receiving electric signals from each portion.

7. The piezoelectric sensor of claim 6, further comprising a wire connected to the insulator layer for receiving electric signal from the insulator layer.

8. The piezoelectric sensor of claim 7, further comprising a signal amplifier connected to the wires.

9. The piezoelectric sensor of claim 8, further comprising a covering material extending over the sensor and amplifier.

10. The piezoelectric sensor of claim 2, wherein the insulator layer and insulator strip are connected to one another.

11. The piezoelectric sensor of claim 2, wherein the insulator layer and insulator strip are brass.

12. The piezoelectric sensor of claim 2, wherein the first and second portions are ceramic.

13. A base for supporting a piezoelectric sensor against a floor of a cage configured to contain a live subject, the base comprising:
    a generally planar support frame having an upper side, a lower side, and an opening defined between the upper side and lower side, wherein the upper side and the cage include one or more features which cooperate to seat and at least partially secure the cage on the support frame whereby the floor of the cage is in contact with the upper side of the support frame;
    a housing mounted in the opening, the housing including an upper portion and a lower portion, the upper portion including a sensor disposed therein and the lower portion includes a biasing member in contact with the sensor, wherein the sensor is biased by the biasing force of the biasing member against the upper portion of the housing, whereby the upper portion is in turn continuously biased by the biasing force against the floor of the cage seated on the support frame, wherein the sensor comprises:
    an insulator layer having opposing upper and lower surfaces;
    a first piezoelectric portion having a lower surface in contact with the upper surface of the insulator layer;
    a second piezoelectric portion having a lower surface in contact with the upper surface of the insulator layer; and
    an insulator strip dividing the first and second piezoelectric portions, wherein the first portion and second piezoelectric portion are laterally positioned with respect to one another in the same generally planar layer.

* * * * *